US010017727B2

(12) United States Patent
Soma et al.

(10) Patent No.: US 10,017,727 B2
(45) Date of Patent: Jul. 10, 2018

(54) METHOD FOR FERMENTATION AND CULTURE, FERMENTED PLANT EXTRACT, FERMENTED PLANT EXTRACT COMPOSITION, METHOD FOR PRODUCING LIPOPOLYSACCHARIDE AND LIPOPOLYSACCHARIDE

(75) Inventors: Gen-Ichiro Soma, Tokyo (JP); Chie Kohchi, Hiroshima (JP); Hiroyuki Inagawa, Shimonoseki (JP); Takashi Nishizawa, Tokushima (JP)

(73) Assignees: Gen-Ichiro Soma, Tokyo (JP); BioMedical Research Group Inc., Tokyo (JP)

( * ) Notice: Subject to any disclaimer, the term of this patent is extended or adjusted under 35 U.S.C. 154(b) by 919 days.

(21) Appl. No.: 12/085,549

(22) PCT Filed: Nov. 28, 2006

(86) PCT No.: PCT/JP2006/323625
§ 371 (c)(1),
(2), (4) Date: Dec. 31, 2008

(87) PCT Pub. No.: WO2007/061102
PCT Pub. Date: May 31, 2007

(65) Prior Publication Data
US 2009/0162344 A1    Jun. 25, 2009

(30) Foreign Application Priority Data

Nov. 28, 2005  (JP) ................................. 2005-342971

(51) Int. Cl.
| A61K 36/03 | (2006.01) |
| C12N 1/20 | (2006.01) |
| A23G 3/48 | (2006.01) |
| A61K 36/48 | (2006.01) |
| A61K 36/899 | (2006.01) |
| C12P 19/04 | (2006.01) |
| A23L 33/10 | (2016.01) |
| A23L 33/105 | (2016.01) |

(52) U.S. Cl.
CPC ................. *C12N 1/20* (2013.01); *A23G 3/48* (2013.01); *A23L 33/10* (2016.08); *A23L 33/105* (2016.08); *A61K 36/03* (2013.01); *A61K 36/48* (2013.01); *A61K 36/899* (2013.01); *C12P 19/04* (2013.01)

(58) Field of Classification Search
None
See application file for complete search history.

(56) References Cited

U.S. PATENT DOCUMENTS

| 2,846,804 A | * | 8/1958 | Elliott ................... A01K 91/02 43/25 |
| 2003/0108573 A1 | | 6/2003 | Proppert et al. |
| 2003/0108617 A1 | * | 6/2003 | Leithe et al. ................. 424/535 |
| 2007/0172492 A1 | | 7/2007 | Soma et al. |

FOREIGN PATENT DOCUMENTS

| CA | 2184084 A1 | 8/1995 |
| EA | 005217 | 12/2004 |
| EP | 0 477 050 A2 | 3/1992 |
| EP | 1410794 A1 | 4/2004 |
| EP | 1645268 A1 | 4/2006 |
| EP | 1 961 823 A1 | 8/2008 |
| JP | 61-146142 A | 7/1986 |
| JP | 01-256376 A | 10/1989 |
| JP | 2-9385 A | 1/1990 |
| JP | 03-061475 A | 3/1991 |
| JP | 04-049240 A | 2/1992 |
| JP | 04-099481 A | 3/1992 |
| JP | 06-009323 A | 1/1994 |
| JP | 06-078756 A | 3/1994 |
| JP | 06-090745 A | 4/1994 |
| JP | 06-141849 A | 5/1994 |
| JP | 06-263650 A | 9/1994 |
| JP | 08-245702 A | 9/1996 |
| JP | 08-337512 A | 12/1996 |
| JP | 10-502802 A | 3/1998 |
| JP | 10-101690 A | 4/1998 |
| JP | 10-286083 A | 10/1998 |
| JP | 2001-178428 A | 7/2001 |
| JP | 2003-033169 A | 2/2003 |
| JP | 2004-059549 A | 2/2004 |
| JP | 2004-154045 A | 6/2004 |
| JP | 2004-222684 A | 8/2004 |
| JP | 2004-321051 A | 11/2004 |
| JP | 2005-198645 A | 7/2005 |
| NZ | 227160 A | 6/1991 |

(Continued)

OTHER PUBLICATIONS

Marshall et al., On the Presence of Acetobacter oxydans in Apple Juice, 1952, J. Gen. Microbiology, 6: 377-381.*

(Continued)

*Primary Examiner* — Terry A McKelvey
*Assistant Examiner* — Catheryne Chen
(74) *Attorney, Agent, or Firm* — Locke Lord LLP

(57) ABSTRACT

In order to provide a method for culturing an immunopotentiator-containing organism having the experience of being eaten, inexpensively without requiring usage of a component derived from an animal, *Acetobacter, Gluconobacter, Xanthomonas, Zymomonas* or *Enterobacter* which is an edible gram-negative bacterium having an immunopotentiation function is cultured using a culture solution composed mainly of wheat or bean curd refuse. Thereby, *Acetobacter* can be obtained inexpensively and safely, and also a low molecular weight lipopolysaccharide which is the immunopotentiator can be obtained inexpensively and safely. Furthermore, no impurity derived from animal components is mixed.

6 Claims, No Drawings

(56) References Cited

FOREIGN PATENT DOCUMENTS

| | | |
|---|---|---|
| WO | WO-03/004003 A1 | 1/2003 |
| WO | WO-2005/000279 A1 | 1/2005 |
| WO | WO-2005/030938 A1 | 4/2005 |
| WO | WO-2007/061102 A1 | 5/2007 |

OTHER PUBLICATIONS

Letter from the Russian agent dated Mar. 16, 2011 and Office Action issued for the Eurasian Patent Application No. 200801470 and English translation thereof.
Tornabene, T. G. et al., "Characterization of the total extractable lipids of *Zymomonas mobilis* var. *mobilis*," Canadian Journal of Microbiology, vol. 28, No. 10, 1982, pp. 1107-1118.
Dekker, R. F. H. et al., "Isolation of alpha-glucan and lipopolysaccharide fractions from *Acetobacter xylinum*," Archives of Microbiology, vol. 115, No. 3, 1977, pp. 353-357.
Goto, S. et al., "Intradermal administration of lipopolysaccharide in treatment of human cancer," Cancer Immunology and Immunotherapy, Spring-Verlag, Berlin, DE, vol. 42, No. 4, Jan. 1, 1996, pp. 255-261.
Kohchi, C. et al., "Applications of lipopolysaccharide derived from *Pantoea agglomerans* (IP-PA1) for health care based on macrophage network theory," Journal of Bioscience and Bioengineering, Elsevier, Amsterdam, NL, vol. 102, No. 6, Dec. 1, 2006, pp. 485-496.
Supplementary European Search Report dated Sep. 8, 2011, issued for the corresponding European patent application No. 06833429.1.
Koei Hamana et al., "Polyamine Profiles of Some Members of the Alpha Subclass of the Class *Proteobacteria*: Polyamine Analysis of Twenty Recently Described Genera", Microbiol. Cult. Coll., Jun. 2003, vol. 19, No. 1, p. 13-21.
Decision of Rejection dated Dec. 12, 2012, issued against the corresponding JP patent application No. 2007-546528.
Office Action dated Jan. 29, 2014, issued for the Japanese patent application No. 2012-106279.
Hiroyuki Inagawa et al, "Homeostasis as regulated by activated macrophage. II. LPS of plant origin other than wheat flour and their concomitant bacteria," Chem.Pharm.Bull.(1992), vol. 40, No. 4, p. 994-997 and a cover page.
Kazunobu Matsushita et al., "Isolation and characterization of outer and cytoplasmic membranes from spheroplasts of *Acetobacter aceti*," Agric.Biol.Chem. (1985), vol. 49, No. 12, p. 3519-3526 and a cover page.
Jianjun Zhang et al., "Synthesis of β-D-Glcp-(1->2)-[β-D-Ribf-(1->3)-] α-L-Rhap-(1->3)-α-L-Rhap-(1->2)-α-L-Rhap, the repeating unit of the lipopolysaccharide of *Acetobacter diazotrophicus* pal 5," Journal of carbohydrate chemistry (2002), vol. 21, No. 6, p. 579-589 and Abstract (1 page).
Thierry Fontaine et al., "Lipopolysaccharides from six strains of *Acetobacter diazotrophicus*," FEMS Microbilogy Letters (1995), vol. 132, p. 45-50 and a cover page.
Chie Kohchi et al., Natural immunity regulatory action of fermented wheat extract., New Food Industry (2006), vol. 48, No. 9, p. 19-27.
Ulmer, A.J. et al., "Lipopolysaccharide: Structure, Bioactivity, Receptors, and Signal Transduction," Trends in Glycoscience and Glycotechnology (Mar. 2002), vol. 14, No. 76, p. 53-68.
C.O. Starnes, "Coley's toxins in perspective," Nature (1992), vol. 357, p. 11-12.
T. Nishizawa et al., "Homeostasis as regulated by activated macrophage. I. Lipopolysaccharide (LPS) from wheat flour: isolation, purification and some biological activities," Chem.Pharm.Bull. (1992), vol. 40, No. 2, p. 479-483.
Hiroyuki Inagawa et al., "Effects of lipopolysaccharide (LPSw) derived from wheat flour having macrophage activating effect on treatment and prevention of various diseases," Biotherapy (Apr. 1991), vol. 5, no. 4, p. 617-621.
Kiyoshi Takeda et al., "Toll-like receptors in innate immunity," International Immunology (2005), vol. 17, No. 1, p. 1-14.
Seikagaku Jiten 2nd edition, Tokyo Kagaku Dojin (1990), p. 1419.
International Search Report dated Dec. 26, 2006, issued on PCT/JP2006/323625.
Office Action dated Oct. 1, 2014, issued for the Japanese patent application No. 2012-106279 and an English concise explanation of the relevance of the cited references.
Written Opinion of the International Searching Authority dated May 28, 2008, issued on PCT/JP2006/323625.
Office Action dated Jul. 23, 2014, issued for the Japanese patent application No. 2013-049648.
Partial English Translation of Imahori et al. Biochemical Dictionary 3-rd edition, 1998, p. 425, Tokyo-Kagaku-Dojin.
Imahori et al. Biochemical Dictionary 3-rd edition, 1998, p. 425, Tokyo-Kagaku-Dojin and partial English translation.
Office Action dated Jun. 7, 2017, issued for the Japanese patent application No. 2016-127108.
Y Taniguchi et al., "Identification and Characterization of Lipopolysaccharide in Acetic Acid Bacteria", Anticancer Research, vol. 26, 2006, pp. 3997-4002. (cited in the Nov. 27, 2017 EP Communication).
N Qureshi et al., "Diphosphoryl Lipid A Obtained from the Nontoxic Lipopolysaccharide of Rhodopseudomonas sphaeroides Is an Endotoxin Antagonist in Mice", Infection and Immunity, vol. 59, No. 1, 1991, pp. 441-444. (cited in Ihe Nov. 27, 2017 EP Communication).
The Communication dated Nov. 27, 2017, issued against the corresponding European patent application No. 06 833 429.1.
H. Dieter Grimmecke et al., "Structure of the capsular polysaccharide and the O-side-chain of the lipopolysaccharide from *Acetobacter methanolicus* MB 58/4 (IMET 10945), and of oligosaccharides resulting from their degradation by the bacteriophage *Acm*1", Carbohydrate Research, vol. 220, Nov. 11, 1991, pp. 165-172 and English concise explanation of relevance.
Kazuyoshi Kawahara, "The Gram-negative Bacteria without Lipopolysaccharide", Protein, Nucleic Acid and Enzyme, vol. 37, No. 2, 1992, pp. 109-116, information page and English concise explanation of relevance.
Biochemical Dictionary 3rd edition, edited by Kazutomo Imahori et al., Tokyo-Kagaku-Dojin, 1998, p. 1490, information page and English concise explanation of relevance.
Iwanami Biological Dictionary 4-th edition, edited by Ryuichi Yasugi et al., Iwanami-shoten, 1996, p. 1474, information page and English concise explanation.
Appeal Hearing dated Apr. 30, 2014, issued for the Japanese patent application 2007-546528 corresponding to the present US application.

* cited by examiner

METHOD FOR FERMENTATION AND CULTURE, FERMENTED PLANT EXTRACT, FERMENTED PLANT EXTRACT COMPOSITION, METHOD FOR PRODUCING LIPOPOLYSACCHARIDE AND LIPOPOLYSACCHARIDE

TECHNICAL FIELD

The present invention relates to a method for fermentation by edible gram-negative bacteria which contains an immunopotentiator, which is safe when added in pharmaceuticals, quasi drugs, cosmetics, functional foods, feedstuff, fertilizers and bath agents used for plants and animals such as mammals (specifically domestic animals and pet animals) including human beings, birds (specifically domestic chickens and pet birds), amphibians, reptiles, fish (specifically pet fish) and invertebrates, a culture solution containing an immunopotentiator obtained by the fermentation, the immunopotentiator obtained from the culture solution, and an extract obtained by concentrating the immunopotentiator.

BACKGROUND ART

For mammals (specifically domestic animals and pet animals) including human beings, birds (specifically domestic chickens and pet birds), amphibians, reptiles, fish (specifically pet fish) and invertebrates and plants, it is a pressing issue to establish methods for preventing or treating diseases including infection protection techniques. In addition, to accomplish this, methods are strongly required in which no chemical is used, no environmental pollution occurs, no resistant bacteria occurs and no accumulation occurs in human bodies. The present inventors have already discovered for the above problem that an immunopotentiator derived from a natural product safely accomplishes effects for the prevention and treatment of diseases (Non-patent Literature 1). As one example thereof, lipopolysaccharide obtained from *Pantoea agglomerans* which is resident bacteria in wheat can be used (Non-patent Literature 1). It is known that *Limulus*-positive glycolipid has a strong immunoenhancement activity (Non-patent Literature 2). The so-called lipopolysaccharide is also included in this category. The lipopolysaccharide is known to be a major component of a cell outer wall of gram-negative bacteria as well as one of the major ingredients of Coley's vaccination and has a potent immunopotentiation activity (Non-patent Literature 3).

The present inventors have discovered that the *Limulus*-positive glycolipids are present in wheat, a part thereof is the lipopolysaccharide of wheat-symbiotic bacteria and these strongly activate a natural immunity (Non-patent Literature 4). The above two safely and strongly activate the natural immunity by percutaneous or oral administration, and exhibit the effects for the prevention and treatment of a wide range of diseases including infectious diseases (Non-patent Literature 5). Furthermore, the present inventors have reported that not only is a content of the lipopolysaccharide derived from *Pantoea agglomerans* increased by fermenting wheat flour with *Pantoea agglomerans* which is resident bacteria in wheat flour, but also that a fermented wheat extract which is a novel immunopotentiator containing components derived from wheat exerts an infection protection effect as a safe and reliable natural material in place of antibiotic chemicals in the fields of stockbreeding and aquaculture.

A basic structure of the lipopolysaccharide is composed of a lipid referred to as lipid A and various sugars (polysaccharide) covalently bound thereto. A region subsequent to the lipid A is composed of R core which takes a relatively uniform structure in related bacteria followed by an O antigen polysaccharide portion which takes a different structure depending on bacterial species (Non-patent Literature 7). The O antigen also has a repeating structure of the same oligosaccharide which characterizes LPS (lipopolysaccharide) (Non-patent Literature 1). Therefore, the lipopolysaccharide generally forms a mixture having multiple molecular weights. It is also known that the lipopolysaccharide has a different structure depending on a microorganism from which the lipopolysaccharide is derived. For example, the lipopolysaccharide derived from *Salmonella* and the lipopolysaccharide derived from *Escherichia coli* are different in structure and also biological activity. However, because generally it is not easy to determine the structure of lipopolysaccharide, details of the structures and functions of the lipopolysaccharides derived from the gram-negative bacteria are not known. Thus, it is described that the lipopolysaccharide generally has a novel structure based on functional difference.

Meanwhile, it has been demonstrated in recent studies that the lipopolysaccharide activates the natural immunity via TLR4 (Non-patent Literature 6). It has been found that the lipid A portion of the lipopolysaccharide is essential for binding to TLR4 and that the polysaccharide portion largely affects an efficiency of intracellular signal transduction of TLR4. From the above, it is speculated that the difference in cellular response of the lipopolysaccharide indicates the structural difference.

It is important for establishing the usefulness of the lipopolysaccharide to demonstrate that the percutaneous or oral administration of the lipopolysaccharide is reliable and safe. Thus, gram-negative bacteria used in the production and fermentation of foods conventionally was emphasized. That is, if the *Limulus*-positive glycolipid and the lipopolysaccharide are present in gram-negative bacteria used in the production of foods and provided as edible products with fermented products, this fact demonstrates that the *Limulus*-positive glycolipid and the lipopolysaccharide have the experience of being eaten. This is a finding which strongly indicates that the percutaneous or oral administration of the *Limulus*-positive glycolipid or the lipopolysaccharide is reliable and safe, and simultaneously should make it possible to develop new health care products and pharmaceuticals such as cosmetics and foods using these substances.

[Non-patent Literature 1] Chie Kohchi et al., "Natural immunity regulatory action of fermented wheat extract," New Food Industry (2006) Vol. 48, p. 19-27

[Non-patent Literature 2] Ulmer, A. J. et al., "Lipopolysaccharide: Structure, Bioactivity, Receptors, and Signal Transduction." Trends in Glycoscience and Glycotechnology, (2002) Vol. 14, p. 53-68

[Non-patent Literature 3] Stames, C. O., "Coley's toxins in perspective." Nature, (1992) Vol. 357, p. 11-12

[Non-patent Literature 4]: Nishizawa, T. et al., Chem. Pharm. Bull., (1992), Vol. 40, p. 479-483

[Non-patent Literature 5] Inagawa H. et al., "Effects of lipopolysaccharide (LPSW) derived from wheat flour having macrophage activating effect on treatment and prevention of various diseases," Biotherapy, (1991) Vol. 5, p. 617-621

[Non-patent Literature 6] Kiyoshi Takedal, et al., "Toll-like receptors in innate immunity." International Immunology, Vol. 17, p. 1-14

[Non-patent Literature 7] Seikagaku Jiten 2nd edition (1990), Tokyo Kagaku Dojin, p. 1949.

DISCLOSURE OF INVENTION

Problems to be Solved by the Invention

An immunopotentiator is often derived from polysaccharides in mushrooms and seaweeds or gram-positive bacteria such as lactic acid bacteria. Commercially available products of a polysaccharide extract from mushrooms or seaweeds are extremely expensive because it is difficult to obtain materials in large amounts and the cost for extraction is high. Meanwhile, for gram-positive bacteria such as lactic acid bacteria, materials of animals are used for their culture. Thus the cost for the culture is high, and the safety of components of the animals is problematic. On the other hand, to make the immunopotentiator from the microorganism widely and always present in plants, it is useful that the microorganism is efficiently cultured in plant components and a structural component or a product thereof is obtained. As one example, *Pantoea agglomerans* residing in wheat can be acquired safely and inexpensively by culturing it using wheat flour as a medium. Meanwhile, there is almost no experience that gram-negative bacteria is orally ingested consciously. Thus, safety of its oral administration over long periods of time is generally unknown.

However, it has been recognized that it is highly safe to orally administer an extract of *Pantoea agglomerans* cultured with wheat flour. Because *Pantoea agglomerans* always reside in wheat, human beings have ingested it continuously since the start of wheat cultivation. That is, *Pantoea agglomerans* and the components thereof have the experience of being ingested by human beings over long periods of time. In fact, folic acid required for lactic acid bacteria growth of rye breads is supplied by *Pantoea agglomerans* which grows during the fermentation process. Thus, the growth of *Pantoea agglomerans* is essential for producing rye breads. When eating rye bread, a considerable amount of microbial cell components is ingested. As for gram-negative bacteria similarly having the experience of being eaten and capable of being cultured with plant components, *Acetobacter aceti* used for manufacturing vinegars, (1) *Acetobacter xylinum*, (2) *Zymomonas mobilis*, (3) *Xanthomonas campestris* and (4) *Enterobacter cloacae* used for producing (1) nata de coco, (2) tequila, (3) xanthan gum and (4) salapao are available. However, in the process of fermenting these, the cultures of multiple species of bacteria are complicated and a single species of the bacteria does not grow. For example, in the process of manufacturing vinegar, a sugar is first produced by *Aspergillus*, then ethanol is produced by *Saccharomyces* and further the growth of *Acetobacter* occurs. Meanwhile, a single culture of *Acetobacter* alone is performed in an SH (Schramm-Hestrin) medium (glucose 20 g, yeast extract 5 g, polypeptone 5 g, citric acid 1.15 g, disodium hydrogen phosphate 2.7 g and distilled water 1000 ml) which is a standard medium. However, polypeptone is a product by degrading cow milk casein with an enzyme, is a protein derived from cattle, and is expensive, as well as having concerns with regard to safety remains.

Several types of gram-negative bacteria known to be used in the fermentation of food or provided as edible product with a fermented product are currently available. Representatives of these edible products are vinegar, tequila, yogurt and breads. However, it has not been reported that the *Limulus*-positive glycolipid or the lipopolysaccharide is present in the gram-negative bacteria (*Acetobacter, Gluconobacter, Frateuria, Zymomonas* or *Gluconobacter suboxydans*) used in the fermentation of food or provided as an edible product with a fermented product.

In consideration of the above problems, the present invention focuses on the idea that oral administration of gram-negative bacteria having the of being eaten over long periods of time is highly safe, and aims at providing a culture solution obtained by culturing gram-negative bacteria having the experience of being eaten over long periods of time and capable of being cultured with plant components inexpensively, an extract thereof, an extract composition as well as lipopolysaccharide and a method for producing the lipopolysaccharide.

The present invention is focused on lipopolysaccharide which gram-negative bacteria has, which is used in the fermentation of food or used as an edible product with a fermented product and has an immunopotentiation function. An *Acetobacter* group is utilized as a food worldwide as well as has having an immunopotentiation function. It is believed that this immunopotentiation function is derived from lipopolysaccharide which the *Acetobacter* group has. Therefore, it is thought that the *Limulus*-positive glycolipid or the lipopolysaccharide can be extracted from gram-negative bacteria having the immunopotentiation function, other than *Acetobacter* by the same method. Thus, it is obvious that the present invention is not limited to microorganisms described in Examples and can be adapted to other microorganisms such as *Zymomonas* and *Gluconobacter* which are gram-negative bacteria having the immunopotentiation function. Furthermore, because the *Limulus*-positive glycolipid or the lipopolysaccharide provided by the present invention can safely activate the immunity by oral or percutaneous administration, they can be formulated and used in pharmaceuticals, foods including foods having a supplementary or special function, skin care products, feedstuff and pet foods which are widely used for the purpose of maintaining health in animals and plants.

Means for Solving Problems

The method for fermentation and culture of the present invention comprises fermenting a material derived from an edible plant with *Acetobacter, Gluconobacter, Xanthomonas, Zymomonas* or *Enterobacter* which is an edible gram-negative bacterium having an immunopotentiation function and simultaneously culturing said bacterium.

The fermented plant extract of the present invention is obtained by the method for fermentation and culture.

A fermented plant extract powder of the present invention is obtained from the fermented plant extract.

A fermented plant extract composition of the present invention contains the fermented plant extract or the fermented plant extract powder.

The fermented plant extract composition may be a pharmaceutical, a pharmaceutical for animals, a quasi drug, a cosmetic, a food, a functional food, a feedstuff or a bath agent.

The fermented plant extract composition may exhibits an anti-inflammatory bowel disease effect, an anti-allergy disease effect, an analgesic effect, an anti-cancer effect, a cholesterol reduction effect, a blood sugar reduction effect, a natural healing power augmenting effect or an immunoenhancement effect.

A lipopolysaccharide of the present invention is obtained from the bacterium cultured by the method for fermentation and culture.

A method for producing the lipopolysaccharide of the present invention comprises obtaining the lipopolysaccharide from the bacterium cultured by the method for fermentation and culture.

A lipopolysaccharide of the present invention is obtained from *Acetobacter*.

A method for producing the lipopolysaccharide of the present invention comprises obtaining the lipopolysaccharide from *Acetobacter*.

Effect of the Invention

According to the present invention, it is obvious that the *Limulus*-positive glycolipid is contained in an *Acetobacter aceti* extract, an *Acetobacter* cocktail extract and a *Gluconobacter suboxydans* extract, and that the lipopolysaccharide is contained in the *Limulus*-positive glycolipid. This demonstrates that the *Limulus*-positive glycolipid or the lipopolysaccharide is contained in gram-negative bacteria utilized for foods, and leads to providing the lipopolysaccharide in the *Limulus*-positive glycolipid as a safe, reliable and inexpensive immunopotentiator having the experience of being eaten.

The present specification includes the contents described in the specification and/or the drawings of Japanese Patent Application No. 2005-342971 which is a basis of the priority of the present application.

BEST MODES FOR CARRYING OUT THE INVENTION

Hereinafter, preferable examples of the present invention will be described in detail below.

Example 1

Fermented Plant Extract Containing *Limulus*-Positive Glycolipid of *Acetobacter*

Fermented Plant Immunopotentiation Extract Obtained by Fermenting Plant Component Alone with *Acetobacter*
(1) Fermented Wheat Extract
A. Production
Culture of Various *Acetobacter* Species with Wheat Wheat flour (0.5 g) and salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make a total volume 100 ml. This was sterilized using an autoclave. One colony of *Acetobacter aceti* or 0.1 ml of *Acetobacter* cocktail or one colony of *Gluconobacter suboxydans* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. A content of the glycolipid contained in this supernatant was measured by endospecy.

B. Physical Property and Biological Activity
*Limulus* Reaction

As a result of measuring the content of the glycolipid in each *Acetobacter* fermented wheat extract by endospecy, it was found that about 18 µg, 56 µg and 43 µg of the glycolipids were extracted per wet solid weight 1 g of the *Acetobacter aceti* fermented wheat extract, the *Acetobacter* cocktail fermented wheat extract and the *Gluconobacter suboxydans* fermented wheat extract, respectively.

Starch Iodine Reaction

Components derived from wheat are also contained in each fermented wheat extract, and are different from the purified lipopolysaccharide derived from *Acetobacter*. In order to demonstrate this, a starch iodine reaction was used. Each fermented wheat extract was positive for the starch iodine reaction, however, the purified lipopolysaccharide derived from *Acetobacter* did not react. That is, both sides are not identical.

Production of Tumor Necrosis Factor (TNF) and Production of Nitrogen Oxide (NO) by Various *Acetobacter* Fermented Wheat Extracts and Inhibition Thereof by Polymyxin B Activation of macrophage lineage cultured cells by the present various fermented wheat extracts was investigated by measuring the production of TNF or NO as an indicator. Furthermore, it was investigated whether this activation was inhibited by polymyxin B which was an inhibitor of the lipopolysaccharide.

The added amounts of the *Acetobacter aceti* fermented wheat extract, the *Acetobacter* cocktail fermented wheat extract and the *Gluconobacter suboxydans* fermented wheat extract are represented by numerical values in terms of an LPSp (lipopolysaccharide of *Pantoea agglomerans*) amount converted based on the result of the *Limulus* reaction. For the TNF production, similar to the case of LPSp, the production of TNF at 10 U/ml or more in a concentration dependent manner was observed when the *Acetobacter* fermented wheat extract was added at a concentration of 100 ng/ml or more in terms of an LPSp concentration.

For the NO production, similar to the case of LPSp, the production of NO at 10 µM/ml or more in the concentration dependent manner was observed when the *Acetobacter aceti* fermented wheat extract, the *Acetobacter* cocktail fermented wheat extract or the *Gluconobacter suboxydans* fermented wheat extract was added at a concentration of 100 ng/ml or more in terms of an LPSp concentration.

It was investigated in the NO production whether the macrophage activation by the *Acetobacter aceti* fermented wheat extract, the *Acetobacter* cocktail fermented wheat extract or the *Gluconobacter suboxydans* fermented wheat extract was inhibited or not by polymyxin B which was the inhibitor of the lipopolysaccharide. As was the case with LPSp, the NO production was almost completely inhibited by the addition of polymyxin B when any of the *Acetobacter* fermented wheat extracts examined was added at a concentration of 100 ng/ml in terms of an LPSp concentration.

(2) *Acetobacter* Fermented Bean Curd Refuse Extract
A. Production

Dry bean curd refuse (0.5 g) and salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Acetobacter aceti* or 0.1 ml of *Acetobacter* cocktail or one colony of *Gluconobacter suboxydans* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

Limulus Reaction

As a result of measuring the content of the glycolipid in each *Acetobacter* fermented bean curd refuse extract by endospecy, it was found that about 4 μg, 23 μg and 21 μg of the glycolipids were extracted per wet solid weight 1 g of the *Acetobacter aceti* fermented bean curd refuse extract, the *Acetobacter* cocktail fermented bean curd refuse extract and the *Gluconobacter suboxydans* fermented bean curd refuse extract, respectively.

Xanthoprotein Reaction

Components derived from the bean curd refuse are also contained in each *Acetobacter* fermented bean curd refuse extract, and are different from the purified lipopolysaccharide derived from *Acetobacter*. In order to demonstrate this, a xanthoprotein reaction was used. A fermented bean curd refuse extract was positive for the xanthoprotein reaction, however, the purified LPS derived from *Acetobacter* did not react. That is, both sides are not identical.

Production of Tumor Necrosis Factor (TNF) and Production of Nitrogen Oxide (NO) by Various *Acetobacter* Fermented Bean Curd Refuse Extracts and Inhibition Thereof by Polymyxin B Activation of macrophage lineage cultured cells by the present various *Acetobacter* fermented bean curd refuse extracts was investigated by measuring the production of TNF or NO as the indicator. Furthermore, it was investigated whether this activation was inhibited by polymyxin B which was the inhibitor of the lipopolysaccharide.

The added amounts of the *Acetobacter aceti* fermented bean curd refuse extract, the *Acetobacter* cocktail fermented bean curd refuse extract and the *Gluconobacter suboxydans* fermented bean curd refuse extract are represented by numerical values in terms of an LPSp amount converted based on the result of the *Limulus* reaction. For the TNF production, similar to the case of LPSp, the production of TNF at 10 U/ml or more in the concentration dependent manner was observed when the *Acetobacter* fermented bean curd refuse extract was added at a concentration of 100 ng/ml or more in terms of an LPSp concentration.

For the NO production, the production of NO at 10 μM/ml or more in the concentration dependent manner was observed when the *Acetobacter aceti* fermented bean curd refuse extract, the *Acetobacter* cocktail fermented bean curd refuse extract or the *Gluconobacter suboxydans* fermented bean curd refuse extract was added at a concentration of 100 ng/ml or more in terms of an LPSp concentration.

It was investigated in the NO production whether the macrophage activation by the *Acetobacter aceti* fermented bean curd refuse extract, the *Acetobacter* cocktail fermented bean curd refuse extract or the *Gluconobacter suboxydans* fermented bean curd refuse extract was inhibited or not by polymyxin B which was the inhibitor of the lipopolysaccharide. As was the case with LPSp, the NO production was almost completely inhibited by the addition of polymyxin B when any of the *Acetobacter* fermented bean curd refuse extracts examined was added at a concentration of 100 ng/ml in terms of an LPSp concentration.

(3) *Acetobacter* Fermented Brown Seaweed Extract

A. Production

Dry "mekabu" (sporophyll of brown seaweed) powder (0.5 g) and salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Acetobacter aceti* or 0.1 ml of *Acetobacter* cocktail or one colony of *Gluconobacter suboxydans* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

Limulus Reaction

As a result of measuring the content of the glycolipid in each *Acetobacter* fermented brown seaweed extract by endospecy, it was found that about 17 μg, 62 μg and 46 μg of the glycolipids were extracted per wet solid weight 1 g of the *Acetobacter aceti* fermented brown seaweed extract, the *Acetobacter* cocktail fermented brown seaweed extract and the *Gluconobacter suboxydans* fermented brown seaweed extract, respectively.

Reaction to β-Glucan

Components derived from the brown seaweed are also contained in each *Acetobacter* fermented brown seaweed extract, and are different from the purified lipopolysaccharide derived from *Acetobacter*. In order to demonstrate this, a reaction to β-glucan using Fungitec G Test MK (Seikagaku Corporation) was used. Each *Acetobacter* fermented brown seaweed extract was positive for the β-glucan reaction, however, the purified LPS derived from *Acetobacter* did not react. That is, both sides are not identical.

Production of Tumor Necrosis Factor (TNF) and Production of Nitrogen Oxide (NO) by Various *Acetobacter* Fermented Brown Seaweed Extracts and Inhibition Thereof by Polymyxin B Activation of macrophage lineage cultured cells by the present various *Acetobacter* fermented brown seaweed extracts was investigated by measuring the production of TNF or NO as an indicator. Furthermore, it was investigated whether this activation was inhibited by polymyxin B which was the inhibitor of the lipopolysaccharide.

The added amounts of the *Acetobacter aceti* fermented brown seaweed extract, the *Acetobacter* cocktail fermented brown seaweed extract and the *Gluconobacter suboxydans* fermented brown seaweed extract are represented by numerical values in terms of an LPSp amount converted based on the result of the *Limulus* reaction. For the TNF production, similar to the case of LPSp, the production of TNF at 10 U/ml or more in the concentration dependent manner was observed when the *Acetobacter* fermented brown seaweed extract was added at a concentration of 100 ng/ml or more in terms of an LPSp concentration.

As for the NO production, the production of NO at 10 μM/ml or more in the concentration dependent manner was observed when the *Acetobacter aceti* fermented brown seaweed extract, the *Acetobacter* cocktail fermented brown seaweed extract or the *Gluconobacter suboxydans* fermented brown seaweed extract was added at a concentration of 100 ng/ml or more in terms of an LPSp concentration.

It was investigated in the NO production whether the macrophage activation by the *Acetobacter aceti* fermented brown seaweed extract, the *Acetobacter* cocktail fermented brown seaweed extract or the *Gluconobacter suboxydans* fermented brown seaweed extract was inhibited or not by polymyxin B which was the inhibitor of the lipopolysaccharide. As was the case with LPSp, the NO production was almost completely inhibited by the addition of polymyxin B when any of the *Acetobacter* fermented brown seaweed extracts examined was added at a concentration of 100 ng/ml in terms of an LPSp concentration.

(4) Example of Practical Application of Various *Acetobacter aceti* Fermented Plant Extracts to Functional Foods Production of Candies Containing Various *Acetobacter aceti* Fermented Plant Extracts As materials, granulated sugar, thick malt syrup, water and each *Acetobacter aceti* fermented plant extract (*Acetobacter aceti* wheat, bean curd refuse or fermented brown seaweed extract) produced in the example were mixed at a ratio of 5:5:5:1, and the mixture was heated at 120 to 160° C. to be boiled down. The boiled down mixture was cooled on a steel plate for cooling, and stretched into a bar shape and molded into grain shapes having a weight of around 1 g to afford candies.

An appropriate amount of these candies was placed in 20 ml of water and dissolved by heating. Measuring the amount of lipopolysaccharide as an active component of the *Acetobacter* fermented plant extract in this solution, the amounts were 3.5 µg/g, 3.1 µg/g and 2.4 µg/g for the *Acetobacter aceti* fermented wheat extract, the *Acetobacter aceti* fermented bean curd refuse extract and the *Acetobacter aceti* fermented brown seaweed extract, respectively. This candy was ingested by 6 men and women having a sore throat due to a cold. Immediately after, a survey related to the sore throat was carried out. As for the sore throat, all 6 persons felt that the sore throat was alleviated with each *Acetobacter aceti* fermented plant extract (one specimen sign test: p<0.03).

(5) Example for Drug Efficacy of Various *Acetobacter aceti* Fermented Plant Extracts Inhibitory Effect of Each *Acetobacter aceti* Fermented Plant Extract on Atopic Dermatitis In order to examine the effect of each *Acetobacter aceti* fermented plant extract on atopic dermatitis, a type I allergy model was introduced. Anti-dinitrophenyl murine monoclonal antibody (1 µg/mouse) was intravenously injected in 5 male BALB/c mice in one group. After one hour, the *Acetobacter aceti* fermented wheat extract, the *Acetobacter aceti* fermented bean curd refuse extract or the *Acetobacter aceti* fermented brown seaweed extract (each 50 µl/mouse) produced in the example was abdominal-intracutaneously administered. After an additional one hour, 20 µl of a mixed solution of 0.25% dinitrofluorobenzene-containing acetone and olive oil (4:1) was applied as an allergen to a surface and a backside of an ear pinna in the mice. The thickness of the ear pinna was measured 1, 2, 24 and 48 hours after the application using a thickness gauge, and a difference (Δ) of the thickness from the thickness just before the application was rendered the degree of edema. The drug administration efficacy was evaluated by an inhibition ratio=(1−Δ pinna edema after the drug administration/Δ pinna edema in control)×100 obtained in an early response observed one hour after the administration of the allergen and a delayed response induced after 24 hours. Results are shown in the Table. As is evident from the Table, the *Acetobacter aceti* fermented wheat extract, the *Acetobacter aceti* fermented bean curd refuse extract and the *Acetobacter aceti* fermented brown seaweed extract inhibited the allergy response.

[Table 1]

TABLE 1

Inhibitory effect of various *Acetobacter aceti* fermented plant extracts on allergy reaction

| Method for administration of extract | Inhibition ratio (%) (after one hour) | Inhibition ratio (%) (after 24 hours) |
|---|---|---|
| Fermented wheat extract | 83.3 | 85.3 |
| Fermented bean curd refuse extract | 89.4 | 78.9 |
| Fermented brown seaweed extract | 75.1 | 98.2 |

Example 2

Fermented Plant Extract Containing *Limulus*-Positive Glycolipid of *Xanthomonas*

Fermented Plant Immunopotentiation Extract Obtained by Fermenting Plant Component Alone with *Xanthomonas*

(1) Fermented Wheat Extract

A. Production

Culture of *Xanthomonas* with Wheat

The wheat flour (0.5 g) and the salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Xanthomonas campestris* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

*Limulus* Reaction

As a result of measuring the content of the glycolipid in *Xanthomonas* fermented wheat extract by endospecy, it was found that about 2.2 mg of the glycolipids were extracted per wet solid weight 1 g of the *Xanthomonas campestris* extract Starch Iodine Reaction Components derived from wheat are also contained in the *Xanthomonas* fermented wheat extract, and are different from the purified lipopolysaccharide derived from *Xanthomonas*. In order to demonstrate this, a starch iodine reaction was used. The fermented wheat extract was positive for the starch iodine reaction, however, the purified lipopolysaccharide derived from *Xanthomonas* did not react. That is, both sides are not identical.

Production of Tumor Necrosis Factor (TNF) and Production of Nitrogen Oxide (NO) by *Xanthomonas* Fermented Wheat Extracts and Inhibition Thereof by Polymyxin B Activation of macrophage lineage cultured cells by the *Xanthomonas* fermented wheat extracts was investigated by measuring the production of TNF or NO as an indicator.

Furthermore, it was investigated whether this activation was inhibited by polymyxin B which was the inhibitor of the lipopolysaccharide.

The added amount of the *Xanthomonas campestris* extract is represented by a numerical value in terms of an LPSp amount converted based on the result of the *Limulus* reaction. For the TNF production, similar to the case of LPSP, the production of TNF at 10 U/ml or more in the concentration dependent manner was observed when the *Xanthomonas* fermented wheat extract was added at a concentration of 10 ng/ml or more in terms of an LPSp concentration.

As for the NO production, the production of NO at 10 µM/ml or more in the concentration dependent manner was observed when the *Xanthomonas* fermented wheat extract was added at a concentration of 10 ng/ml or more in terms of an LPSp concentration.

It was investigated in the NO production whether the macrophage activation by the *Xanthomonas* fermented wheat extract was inhibited or not by polymyxin B which was the inhibitor of the lipopolysaccharide. As was the case with LPSp, the NO production was almost completely inhibited by the addition of polymyxin B when the *Xanthomonas* fermented wheat extract was added at a concentration of 10 ng/ml in terms of an LPSp concentration.

(2) *Xanthomonas* Fermented Bean Curd Refuse Extract

A. Production

The dry bean curd refuse (0.5 g) and the salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Xanthomonas campestris* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

*Limulus* Reaction

As a result of measuring the content of the glycolipid in *Xanthomonas* fermented bean curd refuse extract by endospecy, it was found that about 1.6 mg of the glycolipids were extracted per wet solid weight 1 g of the *Xanthomonas campestris* extract Xanthoprotein Reaction Components derived from the bean curd refuse are also contained in the *Xanthomonas* fermented bean curd refuse extract, and are different from the purified lipopolysaccharide derived from *Xanthomonas*. In order to demonstrate this, xanthoprotein reaction was used. A fermented bean curd refuse extract was positive for the xanthoprotein reaction, however, the purified LPS derived from *Xanthomonas* did not react. That is, both sides are not identical.

Production of Tumor Necrosis Factor (TNF) and Production of Nitrogen Oxide (NO) by *Xanthomonas* Fermented Bean Curd Refuse Extracts and Inhibition Thereof by Polymyxin B Activation of macrophage lineage cultured cells by the *Xanthomonas* fermented bean curd refuse extracts was investigated by measuring the production of TNF or NO as an indicator. Furthermore, it was investigated whether this activation was inhibited by polymyxin B which was the inhibitor of the lipopolysaccharide.

The added amount of the *Xanthomonas campestris* bean curd refuse extract is represented by numerical values in terms of an LPSp amount converted based on the result of the *Limulus* reaction. For the TNF production, similar to the case of LPSp, the production of TNF at 10 U/ml or more in the concentration dependent manner was observed when the *Xanthomonas* fermented bean curd refuse extract was added at a concentration of 10 ng/ml or more in terms of an LPSp concentration.

As for the NO production, the production of NO at 10 µM/ml or more in the concentration dependent manner was observed when the *Xanthomonas* fermented bean curd refuse extract was added at a concentration of 10 ng/ml or more in terms of an LPSp concentration.

It was investigated in the NO production whether the macrophage activation by the *Xanthomonas* fermented bean curd refuse extract was inhibited or not by polymyxin B which was the inhibitor of the lipopolysaccharide. As was the case with LPSp, the NO production was almost completely inhibited by the addition of polymyxin B when the *Xanthomonas* fermented bean curd refuse extract was added at a concentration of 10 ng/ml in terms of an LPSp concentration.

(3) *Xanthomonas* Fermented Brown Seaweed Extract

A. Production

The dry mekabu powder (0.5 g) and the salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Xanthomonas campestris* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

*Limulus* Reaction

As a result of measuring the content of the glycolipid in *Xanthomonas* fermented brown seaweed extract by endospecy, it was found that about 2.2 mg of the glycolipids were extracted per wet solid weight 1 g of the *Xanthomonas campestris* brown seaweed extract.

Reaction to β-Glucan

Components derived from the brown seaweed are also contained in the *Xanthomonas* fermented brown seaweed extract, and are different from the purified lipopolysaccharide derived from *Xanthomonas*. In order to demonstrate this, a reaction to β-glucan using Fungitec G Test MK (Seikagaku Corporation) was used. The *Xanthomonas* fermented brown seaweed extract was positive for the β-glucan reaction, however, the purified LPS derived from *Xanthomonas* did not react. That is, both sides are not identical.

Production of Tumor Necrosis Factor (TNF) and Production of Nitrogen Oxide (NO) by *Xanthomonas* Fermented Brown Seaweed Extracts and Inhibition Thereof by Polymyxin B Activation of macrophage lineage cultured cells by the *Xanthomonas* fermented brown seaweed extracts was investigated by measuring the production of TNF or NO as an indicator. Furthermore, it was investigated whether this activation was inhibited by polymyxin B which was the inhibitor of the lipopolysaccharide.

The added amount of the *Xanthomonas campestris* extract is represented by a numerical value in terms of an LPSp amount converted based on the result of the *Limulus* reaction. For the TNF production, similar to the case of LPSp, the production of TNF at 10 U/ml or more in the concentration dependent manner was observed when the *Xanthomonas* fermented brown seaweed extract was added at a concentration of 10 ng/ml or more in terms of an LPSp concentration.

As for the NO production, the production of NO at 10 µM/ml or more in the concentration dependent manner was observed when the *Xanthomonas* fermented brown seaweed extract was added at a concentration of 10 ng/ml or more in terms of an LPSp concentration.

It was investigated in the NO production whether the macrophage activation by the *Xanthomonas* fermented brown seaweed extract was inhibited or not by polymyxin B which was the inhibitor of the lipopolysaccharide. As was the case with LPSp, the NO production was almost completely inhibited by the addition of polymyxin B when the *Xanthomonas* fermented brown seaweed extract was added at a concentration of 10 ng/ml in terms of an LPSP concentration.

(4) Example of Practical Application of Various *Xanthomonas* Fermented Plant Extracts to Functional Foods Production of Candies Containing Various *Xanthomonas* Fermented Plant Extracts As the materials, granulated sugar, thick malt syrup, water and each *Xanthomonas* fermented plant extract (*Xanthomonas* wheat, bean curd refuse or fermented brown seaweed extract) produced in the example were mixed at a ratio of 5:5:5:1, and the mixture was heated at 120 to 160° C. to be boiled down. The boiled down mixture was cooled on the steel plate for cooling, and stretched into a bar shape and molded into grain shapes having a weight of around 1 g to afford candies.

The appropriate amount of these candies was placed in 20 ml of water and dissolved by heating. Measuring the amount of lipopolysaccharide as the active component of the *Xanthomonas* fermented plant extract in this solution, the amounts were 3.5 µg/g, 3.1 µg/g and 2.4 µg/g for the *Xanthomonas* fermented wheat extract, the *Xanthomonas* fermented bean curd refuse extract and the *Xanthomonas* fermented brown seaweed extract, respectively. This candy was ingested by 6 men and women having a sore throat due to a cold. Immediately after, a survey related to the sore throat was carried out. As for the sore throat, all 6 persons felt that the sore throat was alleviated by each *Xanthomonas* fermented plant extract (one specimen sign test: $p<0.03$).

(5) Example for Drug Efficacy of Various *Xanthomonas* Fermented Plant Extracts

Inhibitory Effect of Each *Xanthomonas* Fermented Plant Extract on Atopic Dermatitis In order to examine the effect of each *Xanthomonas* fermented plant extract on atopic dermatitis, the type I allergy model was introduced. Anti-dinitrophenyl murine monoclonal antibody (1 µg/mouse) was intravenously injected in 5 male BALB/c mice in one group. After one hour, the *Xanthomonas* fermented wheat extract, the *Xanthomonas* fermented bean curd refuse extract or the *Xanthomonas* fermented brown seaweed extract (each 50 µl/mouse) produced in the example was abdominal-intracutaneously administered. After an additional one hour, 20 µl of a mixed solution of 0.25% dinitrofluorobenzene-containing acetone and olive oil (4:1) was applied as the allergen to the surface and the backside of the ear pinna in the mice. The thickness of the ear pinna was measured 1, 2, 24 and 48 hours after the application using a thickness gauge, and the difference (Δ) of the thickness from the thickness just before the application was rendered the degree of edema. The drug administration efficacy was evaluated by an inhibition ratio= (1−Δ pinna edema after the drug administration/Δ pinna edema in control)×100 obtained in an early response observed one hour after the administration of the allergen and a delayed response induced after 24 hours. Results are shown in the Table. As is evident from the Table, the *Xanthomonas* fermented wheat extract, the *Xanthomonas* fermented bean curd refuse extract and the *Xanthomonas* fermented brown seaweed extract inhibited the allergy response.

[Table 2]

TABLE 2

Inhibitory effect of various *Xanthomonas* fermented plant extracts on allergy reaction

| Method for administration of extract | Inhibition ratio (%) (after one hour) | Inhibition ratio (%) (after 24 hours) |
|---|---|---|
| Fermented wheat extract | 77.0 | 95.3 |
| Fermented bean curd refuse extract | 85.2 | 100 |
| Fermented brown seaweed extract | 90.3 | 88.4 |

Example 3

Fermented Plant Extract Containing *Limulus*-Positive Glycolipid of *Enterobacter*

Fermented Plant Immunopotentiation Extract Obtained by Fermenting Plant Component Alone with *Enterobacter*

(1) Fermented Wheat Extract

A. Production

Culture of *Enterobacter* with Wheat

The wheat flour (0.5 g) and the salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Enterobacter cloacae* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

*Limulus* Reaction

As a result of measuring the content of the glycolipid in *Enterobacter* fermented wheat extract by endospecy, it was found that about 1.9 mg of the glycolipids were extracted per wet solid weight 1 g of the *Enterobacter cloacae* extract.

Starch Iodine Reaction

Components derived from wheat are also contained in the *Enterobacter* fermented wheat extract, and are different from the purified lipopolysaccharide derived from *Enterobacter*. In order to demonstrate this, a starch iodine reaction was used. The fermented wheat extract was positive for the starch iodine reaction, however, the purified lipopolysaccharide derived from *Enterobacter* did not react. That is, both sides are not identical.

Production of Tumor Necrosis Factor (TNF) and Production of Nitrogen Oxide (NO) by *Enterobacter* Fermented Wheat Extracts and Inhibition Thereof by Polymyxin B Activation of macrophage lineage cultured cells by the *Enterobacter* fermented wheat extracts was investigated by measuring the production of TNF or NO as an indicator. Furthermore, it was investigated whether this activation was inhibited by polymyxin B which was the inhibitor of the lipopolysaccharide.

The added amount of the *Enterobacter cloacae* extract is represented by a numerical value in terms of an LPSp amount converted based on the result of the *Limulus* reaction. For the TNF production, similar to the case of LPSp, the production of TNF at 10 U/ml or more in the concentration dependent manner was observed when the *Enterobacter* fermented wheat extract was added at a concentration of 10 ng/ml or more in terms of an LPSp concentration.

As for the NO production, the production of NO at 10 μM/ml or more in the concentration dependent manner was observed when the *Enterobacter* fermented wheat extract was added at a concentration of 10 ng/ml or more in terms of an LPSp concentration.

It was investigated in the NO production whether the macrophage activation by the *Enterobacter* fermented wheat extract was inhibited or not by polymyxin B which was the inhibitor of the lipopolysaccharide. As was the case with LPSp, the NO production was almost completely inhibited by the addition of polymyxin B when the *Enterobacter* fermented wheat extract was added at a concentration of 10 ng/ml in terms of an LPSp concentration.

(2) *Enterobacter* Fermented Bean Curd Refuse Extract

A. Production

The dry bean curd refuse (0.5 g) and the salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Enterobacter cloacae* was added thereto, which was then left to stand and cultured at 30° C. for 5 days.

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

B. Physical Property and Biological Activity

*Limulus* Reaction

As a result of measuring the content of the glycolipid in *Enterobacter* fermented bean curd refuse extract by endospecy, it was found that about 560 μg of the glycolipids were extracted per wet solid weight 1 g of the *Enterobacter cloacae* extract Xanthoprotein Reaction Components derived from the bean curd refuse are also contained in the *Enterobacter* fermented bean curd refuse extract, and are different from the purified lipopolysaccharide derived from *Enterobacter*. In order to demonstrate this, the xanthoprotein reaction was used. The fermented bean curd refuse extract was positive for a xanthoprotein reaction, however, the purified lipopolysaccharide derived from *Enterobacter* did not react. That is, both sides are not identical.

Production of Tumor Necrosis Factor (TNF) and Production of Nitrogen Oxide (NO) by *Enterobacter* Fermented Bean Curd Refuse Extracts and Inhibition Thereof by Polymyxin B Activation of macrophage lineage cultured cells by the *Enterobacter* fermented bean curd refuse extracts was investigated by measuring the production of TNF or NO as an indicator. Furthermore, it was investigated whether this activation was inhibited by polymyxin B which was the inhibitor of the lipopolysaccharide.

The added amount of the *Enterobacter cloacae* fermented bean curd refuse extract is represented by a numerical value in terms of an LPSp amount converted based on the result of the *Limulus* reaction. For the TNF production, similar to the case of LPSp, the production of TNF at 10 U/ml or more in the concentration dependent manner was observed when the *Enterobacter* fermented bean curd refuse extract was added at a concentration of 10 ng/ml or more in terms of an LPSp concentration.

For the NO production, the production of NO at 10 μM/ml or more in the concentration dependent manner was observed when the *Enterobacter* fermented bean curd refuse extract was added at a concentration of 10 ng/ml or more in terms of an LPSp concentration.

It was investigated in the NO production whether the macrophage activation by the *Enterobacter* fermented bean curd refuse extract was inhibited or not by polymyxin B which was the inhibitor of the lipopolysaccharide. As was the case with LPSp, the NO production was almost completely inhibited by the addition of polymyxin B when the *Enterobacter* fermented bean curd refuse extract was added at a concentration of 10 ng/ml in terms of an LPSp concentration.

(3) *Enterobacter* Fermented Brown Seaweed Extract

A. Production

The dry mekabu powder (0.5 g) and the salts (disodium hydrogen phosphate heptahydrate 1.28 g, potassium dihydrogen phosphate 0.3 g, sodium chloride 50 mg, ammonium chloride 100 mg, 0.2 ml of an aqueous solution of 1 M magnesium sulfate, 0.01 ml of an aqueous solution of 1 M calcium chloride) and water were added to make the total volume 100 ml. This was sterilized using an autoclave. One colony of *Enterobacter cloacae* was added thereto, which was then left to stand and cultured at 30° C. for 5 days.

B. Physical Property and Biological Activity

Extraction with Hot Water (Extract)

A solid content was collected from each culture solution by a centrifuge, an equal volume of distilled water was added to this solid content, and the mixture was heated at 90° C. for 30 minutes using a block heater. After cooling to room temperature, each supernatant was separated by centrifuging at 10,000 rpm for 10 minutes using a microcentrifuge. The content of the glycolipid contained in this supernatant was measured by endospecy.

*Limulus* Reaction

As a result of measuring the content of the glycolipid in *Enterobacter* fermented brown seaweed extract by endospecy, it was found that about 910 μg of the glycolipids were extracted per wet solid weight 1 g of the *Enterobacter cloacae* fermented brown seaweed extract.

Reaction to β-Glucan

Components derived from the brown seaweed are also contained in the *Enterobacter* fermented brown seaweed extract, and are different from the purified lipopolysaccharide derived from *Enterobacter*. In order to demonstrate this, a reaction to β-glucan using Fungitec G Test MK (Seikagaku Corporation) was used. The *Enterobacter* fermented brown seaweed extract was positive for the β-glucan reaction, however, the purified LPS derived from *Enterobacter* did not react. That is, both sides are not identical.

Production of Tumor Necrosis Factor (TNF) and Production of Nitrogen Oxide (NO) by *Enterobacter* Fermented Brown Seaweed Extracts and Inhibition Thereof by Polymyxin B Activation of macrophage lineage cultured cells by the *Enterobacter* fermented brown seaweed extracts was investigated by measuring the production of TNF or NO as an indicator. Furthermore, it was investigated whether this activation was inhibited by polymyxin B which was the inhibitor of the lipopolysaccharide.

The added amount of the *Enterobacter cloacae* extract is represented by a numerical value in terms of an LPSp amount converted based on the result of the *Limulus* reaction. For the TNF production, similar to the case of LPSp, the production of TNF at 10 U/ml or more in the concentration dependent manner was observed when the *Enterobacter* fermented brown seaweed extract was added at a concentration of 10 ng/ml or more in terms of an LPSp concentration.

As for the NO production, the production of NO at 10 μM/ml or more in the concentration dependent manner was observed when the *Enterobacter* fermented brown seaweed extract was added at a concentration of 10 ng/ml or more in terms of an LPSp concentration.

It was investigated in the NO production whether the macrophage activation by the *Enterobacter* fermented brown seaweed extract was inhibited or not by polymyxin B which was the inhibitor of the lipopolysaccharide. As was the case with LPSp, the NO production was almost completely inhibited by the addition of polymyxin B when the *Enterobacter* fermented brown seaweed extract was added at a concentration of 10 ng/ml in terms of an LPSp concentration.

(4) Example of Practical Application of Various *Enterobacter* Fermented Plant Extracts to Functional Foods Production of Candies Containing Various *Enterobacter* Fermented Plant Extracts As the materials, granulated sugar, thick malt syrup, water and each *Enterobacter* fermented plant extract (*Enterobacter* wheat, bean curd refuse or fermented brown seaweed extract) produced in the example were mixed at a ratio of 5:5:5:1, and the mixture was heated at 120 to 160° C. to be boiled down. The boiled down mixture was cooled on the steel plate for cooling, and stretched into a bar shape and molded into grain shapes having a weight around 1 g to afford candies.

The appropriate amount of these candies was placed in 20 ml of water and dissolved by heating. Measuring the amount of lipopolysaccharide as the active component of the *Enterobacter* fermented plant extract in this solution, the amounts were 10.1 μg/g, 8.4 μg/g and 6.8 μg/g for the *Enterobacter* fermented wheat extract, the *Enterobacter* fermented bean curd refuse extract and the *Enterobacter* fermented brown seaweed extract, respectively. This candy was ingested by 6 men and women having a sore throat due to a cold. Immediately after, a survey related to the sore throat was carried out. As for the sore throat, all 6 persons felt that the sore throat was alleviated by each *Enterobacter* fermented plant extract (one specimen sign test: p<0.03).

(5) Example for Drug Efficacy of Various *Enterobacter* Fermented Plant Extracts Inhibitory Effect of Each *Enterobacter* Fermented Plant Extract on Atopic Dermatitis In order to examine the effect of each *Enterobacter* fermented plant extract on atopic dermatitis, the type I allergy model was introduced. Anti-dinitrophenyl murine monoclonal antibody (1 g/mouse) was intravenously injected in 5 male BALB/c mice in one group. After one hour, the *Enterobacter* fermented wheat extract, the *Enterobacter* fermented bean curd refuse extract or the *Enterobacter* fermented brown seaweed extract (each 50 μl/mouse) produced in the example was abdominal-intracutaneously administered. After an additional one hour, 20 ml of a mixed solution of 0.25% dinitrofluorobenzene-containing acetone and olive oil (4:1) was applied as the allergen to the surface and the backside of the ear pinna in the mice. The thickness of the ear pinna was measured 1, 2, 24 and 48 hours after the application using a thickness gauge, and the difference (Δ) of the thickness from the thickness just before the application was rendered the degree of edema. The drug administration efficacy was evaluated by an inhibition ratio=(1−Δ pinna edema after the drug administration/Δ pinna edema in control)×100 obtained in an early response observed one hour after the administration of the allergen and a delayed response induced after 24 hours. Results are shown in the Table. As is evident from the Table, the *Enterobacter* fermented wheat extract, the *Enterobacter* fermented bean curd refuse extract and the *Enterobacter* fermented brown seaweed extract inhibited the allergy response.

[Table 3]

TABLE 3

Inhibitory effect of various *Acetobacter aceti* fermented plant extracts on allergy reaction

| Method for administration of extract | Inhibition ratio (%) (after one hour) | Inhibition ratio (%) (after 24 hours) |
|---|---|---|
| Fermented wheat extract | 64.3 | 87.5 |
| Fermented bean curd refuse extract | 58.7 | 82.7 |
| Fermented brown seaweed extract | 73.2 | 90.1 |

Example 4

*Acetobacter* (*Acetobacter aceti*, *Acetobacter* Cocktail, *Gluconobacter suboxydans*) Lipopolysaccharide The *Acetobacter* species are gram-negative bacteria which are widely used worldwide, are frequently eaten and are essential for manufacturing vinegar. The lipopolysaccharide from *Acetobacter* cultured with an animal material or a plant material has thus far not been known. Its biological activity is also different from those of the known lipopolysaccharides.

(1) *Acetobacter* Lipopolysaccharide Obtained by Ordinary Method for *Acetobacter* Culture A. Production

*Acetobacter aceti* or *Gluconobacter suboxydans* was seeded on an agar medium (polypeptone 5.0 g, yeast extract 5.0 g, glucose 5.0 g, magnesium sulfate heptahydrate 1.0 g and agar 15.0 g/liter), and cultured at 30° C. for two days. One colony of *Acetobacter aceti* or *Gluconobacter suboxydans* or 0.1 ml of *Acetobacter* cocktail was added to a culture flask in which 50 ml of a sterilized liquid medium (polypeptone 5.0 g, yeast extract 5.0 g, glucose 5.0 g and magnesium sulfate heptahydrate 1.0 g/liter) had been added, and left to stand and cultured at 30° C. for 5 days. After culturing for 5 days, 1 ml of cultured bacterial solution was added to 30 culture flasks in which 50 ml of the medium had been added, and left to stand and cultured at 30° C. for 5 days.

Extraction

As an extraction method, Westphal's method was used. Distilled water was added to wet microbial cells of *Acetobacter aceti* or *Gluconobacter suboxydans* or *Acetobacter* cocktail to make a final concentration of 100 mg/ml, and the microbial cells were suspended. An equal volume of 90% phenol solution was added to this suspension, which was then stirred at 65 to 68° C. for 20 minutes. Subsequently, the solution was cooled to 10° C. or below, and centrifuged at 10,000 rpm at 4° C. for 20 minutes using a high speed cooling centrifuge. After the centrifugation, only an upper aqueous layer was transferred to another vessel, and an intermediate layer and a lower phenol layer were returned back to the original vessel, to which distilled water in the same amount as the amount of the collected aqueous layer was added. The resulting solution was stirred again at 65 to 68° C. for 20 minutes. Subsequently, the solution was cooled to 10° C. or below, and centrifuged at 10,000 rpm at 4° C. for 20 minutes using the high speed cooling centrifuge. Only the upper aqueous layer was collected and combined with previously collected aqueous layer. The collected aqueous layer was subjected to ultrafiltration or dialysis for the purpose of removing phenol. The content of glycolipid contained in each extracted solution was measured by endospecy.

B. Physical Property and Biological Activity

The lipopolysaccharide derived from *Acetobacter* was obtained from the *Acetobacter* microbial cells by Westphal's method. In this study, three *Acetobacter* species, i.e., *Acetobacter aceti* which was a representative of *Acetobacter* species, *Acetobacter* cocktail used in manufacturing vinegars, and *Gluconobacter suboxydans* were used. As a result of measuring the content of glycolipid by endospecy, it was found that about 5 mg, 12.5 mg and 10 mg of glycolipids had been extracted per 1 g of the wet microbial cells of *Acetobacter aceti, Acetobacter* cocktail and *Gluconobacter suboxydans*, respectively. For the purpose of investigating the biological activity, the resulting phenol extraction solution was attempted to be further purified. Because major components other than the glycolipid contained in the extraction solution were nucleic acids, first the solution was treated with DNase and subsequently RNase. Then, an equal volume 90% phenol was added. The resulting solution was stirred for 10 minutes, and then centrifuged at 10,000 rpm at 4° C. for 20 minutes using a high speed cooling centrifuge. Only the upper aqueous layer was collected. The collected aqueous layer was subjected to ultrafiltration or dialysis for the purpose of removing phenol.

*Limulus* Reaction

Using an endospecy kit for detecting a lipopolysaccharide-specific reaction and commercially available from Seikagaku Corporation, it was examined whether the *Limulus*-positive glycolipid was contained or not in *Acetobacter aceti, Acetobacter* cocktail and *Gluconobacter suboxydans*. As a result, it was found that about 5 mg, 12.5 mg and 10 mg of the *Limulus*-positive glycolipids were extracted per 1 g of wet microbial cells of *Acetobacter aceti, Acetobacter* cocktail and *Gluconobacter suboxydans*. This demonstrates that the *Limulus*-positive glycolipid is contained in *Acetobacter aceti, Acetobacter* cocktail and *Gluconobacter suboxydans*.

Molecular Weight

SDS-PAGE was carried out for analyzing the molecular weight of the *Limulus*-positive glycolipid (lipopolysaccharide) derived from *Acetobacter aceti* or *Acetobacter* cocktail. As for LPSp, a band was observed around 5,000 which recognized the fact it was low molecular. For the lipopolysaccharide derived from *Acetobacter aceti* or *Acetobacter* cocktail, the band around 5,000 was observed suggesting that these *Limulus*-positive glycolipids (lipopolysaccharide) were low molecular.

Production of TNF and Production of NO, and Inhibition Thereof by Polymyxin B

The activation of macrophage lineage cultured cells by the lipopolysaccharides derived from *Acetobacter aceti* lipopolysaccharide, *Gluconobacter suboxydans* lipopolysaccharide and *Acetobacter* cocktail lipopolysaccharide was examined by measuring the production of TNF or NO as an indicator. Furthermore, it was examined whether this activation was inhibited by polymyxin B which was the inhibitor of the lipopolysaccharide.

The added amounts of the *Acetobacter aceti* lipopolysaccharide, the *Gluconobacter suboxydans* lipopolysaccharide and the *Acetobacter* cocktail lipopolysaccharide are represented by numerical values in terms of an LPSp amount converted based on the result of the *Limulus* reaction. As for the TNF production, similar to the case of LPSp, the production of TNF at 10 U/ml or more in the concentration dependent manner was observed when the *Acetobacter aceti* lipopolysaccharide, the *Gluconobacter suboxydans* lipopolysaccharide or the *Acetobacter* cocktail lipopolysaccharide was added at a concentration of 1000 ng/ml or more in terms of an LPSp concentration.

As for the NO production, the production of NO at 20 μM/ml or more in the concentration dependent manner was observed when the *Acetobacter aceti* lipopolysaccharide, the *Gluconobacter suboxydans* lipopolysaccharide or the *Acetobacter* cocktail lipopolysaccharide was added at a concentration of ng/ml or more in terms of an LPSp concentration.

It was investigated in the NO production whether the macrophage activation by the *Acetobacter* lipopolysaccharide was inhibited or not by polymyxin B which was the inhibitor of the lipopolysaccharide. As was the case with LPSp, the NO production was almost completely inhibited by the addition of polymyxin B when the *Acetobacter aceti* lipopolysaccharide, the *Gluconobacter suboxydans* lipopolysaccharide or the *Acetobacter* cocktail lipopolysaccharide was added at a concentration of 10,000 ng/ml in terms of an LPSp concentration.

TNF Production of TNF Using TLR4 Deleted Macrophages

By using the macrophage cells which deleted TLR4 which was a receptor for the lipopolysaccharide, it was identified that the activation function of the macrophage induced by the *Acetobacter aceti* lipopolysaccharide, the *Gluconobacter suboxydans* lipopolysaccharide or the *Acetobacter* cocktail lipopolysaccharide was attenuated. The lipopolysaccharide transmits the signal to the macrophage cells via TLR4 which is its receptor present on the cell surface. Meanwhile, zymosan which is a yeast cell wall transmits the signal via TLR2 to activate the macrophage cells. Therefore, it is believed that when the macrophage-activating substance contained in *Acetobacter* is the lipopolysaccharide, the signal is not transmitted in the macrophage cells which has deleted TLR4 and as a result, the macrophage activation is attenuated to attenuate the TNF and NO production.

In the macrophage cells deleting TLR4, no TNF production was observed when the *Acetobacter aceti* lipopolysaccharide, the *Gluconobacter suboxydans* lipopolysaccharide or the *Acetobacter* cocktail lipopolysaccharide was added at a concentration of 1000 ng/ml or more in terms of an LPSp concentration. This result means that the macrophage activation was attenuated to attenuate the TNF and NO production. Therefore, it was demonstrated that TLR4 was involved in the macrophage activation by the *Acetobacter aceti* lipopolysaccharide, the *Gluconobacter suboxydans* lipopolysaccharide or the *Acetobacter* cocktail lipopolysaccharide.

Functional Difference Between *Acetobacter* Lipopolysaccharide and Known Lipopolysaccharide The *Acetobacter aceti* lipopolysaccharide and the *Acetobacter* cocktail lipopolysaccharide are completely different from the known lipopolysaccharides, e.g., *Escherichia coli* lipopolysaccharide and *Pantoea agglomerans* lipopolysaccharide in dosage dependency in the TNF production and the NO production. The known lipopolysaccharide, e.g., *Escherichia coli* lipopolysaccharide and *Pantoea agglomerans* lipopolysaccharide at a concentration of 10 ng/ml (in terms of an LPSp concentration based on *Limulus* reaction) indicated the production of TNF at 10 U/ml or more in the concentration dependent manner. Also in the NO production, those at a concentration of 10 ng/ml or more indicated the production of NO at 20 μM/ml or more in the concentration dependent manner. On the other hand, the *Acetobacter aceti* lipopolysaccharide and the *Acetobacter* cocktail lipopolysaccharide at a concentration of 100 ng/ml (in terms of an LPSp concentration based on *Limulus* reaction) did not indicate the TNF production. Also in the NO production the *Acetobacter aceti* lipopolysaccharide and the *Acetobacter* cocktail lipopolysaccharide at the concentration of 1000 ng/ml in terms of an LPSp concentration did not induce the NO production. That is, this indicates that the *Acetobacter* lipopolysaccharides and the known lipopolysaccharides are different in biological activity, and it is considered that the *Acetobacter* lipopolysaccharide is novel as a substance.

(2) Example of Practical Application of *Acetobacter* Lipopolysaccharide to Functional Foods Production of Candies Containing *Acetobacter* Lipopolysaccharide As the materials, granulated sugar, thick malt syrup, water and *Acetobacter aceti* lipopolysaccharide produced in the example 2 were mixed at a ratio of 5:5:5:1, and the mixture was heated at 120 to 160° C. to be boiled down. The boiled down mixture was cooled on the steel plate for cooling, and stretched into a bar shape and molded into grain shapes having the weight of around 1 g to afford candies.

The appropriate amount of these candies was placed in 20 ml of water and dissolved by heating. Measuring the amount of lipopolysaccharide as the active component of the *Acetobacter aceti* in this solution, the amount was 2.1 μg/g. This candy was ingested by 6 men and women having a sore throat due to a cold. Immediately after, a survey related to the sore throat was carried out. As for the sore throat, all 6 persons felt that the sore throat was alleviated (one specimen sign test: p<0.03).

(3) Example for Drug Efficacy of *Acetobacter* Lipopolysaccharide

Inhibitory Effect of *Acetobacter* Lipopolysaccharide on Atopic Dermatitis

In order to examine the effect of the *Acetobacter aceti* lipopolysaccharide on atopic dermatitis, the type I allergy model was introduced. Anti-dinitrophenyl murine monoclonal antibody (1 μg/mouse) was intravenously injected in 5 male BALB/c mice in one group. After one hour, the *Acetobacter aceti* lipopolysaccharide (50 μl/mouse) produced in the example was abdominal-intracutaneously administered. After additional one hour, 20 μl of a mixed solution of 0.25% dinitrofluorobenzene-containing acetone and olive oil (4:1) was applied as the allergen to the surface and the backside of the ear pinna in the mice. The thickness of the ear pinna was measured 1, 2, 24 and 48 hours after the application using a thickness gauge, and the difference (A) of the thickness from the thickness just before the application was rendered the degree of edema. The drug administration efficacy was evaluated by an inhibition ratio=(1−Δ pinna edema after the drug administration/A pinna edema in control)×100 obtained in an early response observed one hour after the administration of the allergen and a delayed response induced after 24 hours. Results are shown in the Table. As is evident from the Table, the *Acetobacter aceti* lipopolysaccharide inhibited the allergy response even by either of the intracutaneous administration or oral administration.

[Table 4]

TABLE 4

Inhibitory effect of *Acetobacter aceti* lipopolysaccharide on allergy reaction

| Method for administration of lipopolysaccharide | Dosage (mouse) | Inhibition ratio (%) (after one hour) | Inhibition ratio (%) (after 24 hours) |
|---|---|---|---|
| Intracutaneous administration | 4 μg | 85.2 | 100 |
| Oral administration | 100 μg | 55.3 | 58.4 |

All publications, patents and patent applications cited herein are incorporated herein in their entities by reference.

The invention claimed is:

1. A method for producing a lipopolysaccharide consisting of the steps of:
   creating a culture medium consisting of a edible plant member selected from the group consisting of wheat flour, dry bean curd refuse, and dry brown seaweed powder; disodium hydrogen phosphate heptahydrate; potassium dihydrogen phosphate; sodium chloride; ammonium chloride; an aqueous solution of magnesium sulfate; an aqueous solution of calcium chloride; and water;
   adding to the culture medium a bacteria selected from a group consisting of *Acetobacter aceti, Gluconobacter, Xanthomonas, Enterobacter* or *Zymomonas;*
   letting the combination of culture medium and bacteria stand to simultaneously ferment and culture, and
   extracting lipopolysaccharide from the culture.

2. The method of claim 1 wherein 100 ml of the culture medium is created in the following proportions: an edible plant member (5 g); disodium hydrogen phosphate heptahydrate (1.28 g); potassium dihydrogen phosphate (0.3 g); sodium chloride (50 mg); ammonium chloride (100 mg); an aqueous solution of magnesium sulfate (0.2 ml); an aqueous solution of calcium chloride (0.01 ml); and water.

3. The method of claim 1 wherein the culture medium and the bacterium is left to stand and culture at 30° C. for 5 days.

4. The method of claim 1 wherein the culture medium is sterilized before the bacteria is added.

5. The method of claim 1 wherein extraction is performed by the steps of centrifugation of the fermented and cultured medium, separating a solid content, adding an equal volume of distilled water, heating the water and solid content at 90° C. for 30 minutes, cooling and centrifugation of the water and solid content.

6. A method for producing a lipopolysaccharide consisting of the steps of:
creating a culture medium consisting of a edible plant member selected from the group consisting of wheat flour and dry brown seaweed powder; disodium hydrogen phosphate heptahydrate; potassium dihydrogen phosphate; sodium chloride; ammonium chloride; an aqueous solution of magnesium sulfate; an aqueous solution of calcium chloride; and water;
adding to the culture medium a bacteria selected from a group consisting of *Acetobacter aceti, Gluconobacter, Xanthomonas, Enterobacter* or *Zymomonas;*
letting the combination of culture medium and bacteria stand to simultaneously ferment and culture, and
extracting lipopolysaccharide from the culture.

* * * * *